(12) United States Patent
Kim et al.

(10) Patent No.: US 9,588,111 B2
(45) Date of Patent: Mar. 7, 2017

(54) MEMBRANE BIOSENSOR HAVING MULTI-HOLE FILM ATTACHED THERETO AND METHOD FOR MEASURING IMMUNOLOGICAL REACTION OR ENZYMATIC REACTION USING THE SAME

(75) Inventors: Min Gon Kim, Daejeon (KR); Yong Beom Shin, Daejeon (KR); Young Kyeng O, Daejeon (KR); Hyo Arm Joung, Daejeon (KR)

(73) Assignee: INGIBIO, LTD., Gwangju (KR)

( * ) Notice: Subject to any disclaimer, the term of this patent is extended or adjusted under 35 U.S.C. 154(b) by 1309 days.

(21) Appl. No.: 13/511,962

(22) PCT Filed: Nov. 24, 2010

(86) PCT No.: PCT/KR2010/008363
§ 371 (c)(1),
(2), (4) Date: May 24, 2012

(87) PCT Pub. No.: WO2011/065751
PCT Pub. Date: Jun. 3, 2011

(65) Prior Publication Data
US 2012/0270235 A1    Oct. 25, 2012

(30) Foreign Application Priority Data

Nov. 24, 2009  (KR) .................. 10-2009-0113779
Nov. 24, 2010  (KR) .................. 10-2010-0117655

(51) Int. Cl.
*C12M 1/34* (2006.01)
*G01N 33/538* (2006.01)
*G01N 33/543* (2006.01)

(52) U.S. Cl.
CPC ..... *G01N 33/538* (2013.01); *G01N 33/54366* (2013.01)

(58) Field of Classification Search
USPC ....... 422/400, 401, 420, 421, 422, 423, 424, 422/425, 426, 427, 428, 429; 435/287.7,
(Continued)

(56) References Cited

U.S. PATENT DOCUMENTS

| 5,219,528 A | 6/1993 | Clark |
| 7,494,818 B1 | 2/2009 | Anaokar et al. |

(Continued)

FOREIGN PATENT DOCUMENTS

| CN | 1564945 A | 1/2005 |
| EP | 0233385 A1 | 8/1987 |

(Continued)

OTHER PUBLICATIONS

Japanese Office Action dated Aug. 19, 2014.
(Continued)

*Primary Examiner* — Chris L Chin
(74) *Attorney, Agent, or Firm* — Hauptman Ham, LLP

(57) ABSTRACT

The present invention relates to a membrane sensor having a multi-hole film attached thereto and a method for measuring immunological reactions or enzymatic reactions using the same. More specifically, the present invention relates to a membrane sensor in which a multi-hole film is joined to the top of a membrane on which receptors are immobilized, and a method for measuring immunological reactions or enzymatic reactions using the same. The present invention makes it possible to adjust the sensitivity of membrane biosensors by adjusting the hole size in the multi-hole film and so makes it possible to measure analytes with a high degree of sensitivity using just a small amount of sample, and makes it possible to simultaneously measure diverse types of analyte by attaching various types of receptor on the membrane sensor.

7 Claims, 12 Drawing Sheets

(58) Field of Classification Search
USPC ... 435/287.8, 287.9, 970; 436/169, 170, 809
See application file for complete search history.

(56) References Cited

U.S. PATENT DOCUMENTS

| | | | |
|---|---|---|---|
| 7,754,439 B2* | 7/2010 | Moore | ............. B01J 19/0046 |
| | | | 435/287.1 |
| 2005/0214161 A1 | 9/2005 | Gupta | |
| 2007/0256941 A1 | 11/2007 | Prasad et al. | |
| 2009/0192297 A1 | 7/2009 | Yoshida et al. | |

FOREIGN PATENT DOCUMENTS

| | | |
|---|---|---|
| EP | 0247850 | 12/1987 |
| EP | 0440350 | 8/1991 |
| EP | 0617284 | 9/1994 |
| EP | 0893690 A1 | 1/1999 |
| GB | 2391068 A | 1/2004 |
| JP | 2006-507511 | 3/2006 |
| JP | 2006189304 A | 7/2006 |
| JP | 2007163140 A | 6/2007 |
| KR | 10-0348351 | 8/2002 |
| KR | 10-0591390 | 8/2004 |
| KR | 10-0599420 | 7/2006 |
| WO | 0192886 A1 | 12/2001 |
| WO | 2009040364 A1 | 4/2009 |

OTHER PUBLICATIONS

European Search Report dated Dec. 13, 2013.
Chinese Office Action dated Feb. 19, 2014.
International Search Report mailed Sep. 1, 2011 for PCT/KR2010/008363.

* cited by examiner

Level 1	Level 2

MEMBRANE BIOSENSOR HAVING MULTI-HOLE FILM ATTACHED THERETO AND METHOD FOR MEASURING IMMUNOLOGICAL REACTION OR ENZYMATIC REACTION USING THE SAME

CROSS REFERENCE TO RELATED APPLICATION

This application claims the priority of Korean Patent Application No. 10-2009-0113779, filed on Nov. 24, 2009, and Korean Patent Application No. 10-2010-0117655, filed on Nov. 24, 2010 in the KIPO (Korean Intellectual Property Office). Further, this application is the National Phase application of International Application No. PCT/KR2010/008363 filed Nov. 24, 2010, which designates the United States and was published in Korean.

TECHNICAL FIELD

The present invention relates to a membrane sensor having a multi-hole film attached thereto and a method for measuring immunological reactions or enzymatic reactions using the same. More specifically, the present invention relates to a membrane sensor capable of rapidly measuring antigen-antibody reaction and a method for measuring immunological reactions or enzymatic reactions using the same.

BACKGROUND ART

A lateral flow assay (LFA) system is generally used to detect antigen-antibody reaction. In the LFA system, antibody is immobilized to a membrane in which a fluid sample moves via capillary force, a conjugate pad and a sample pad are connected to an upstream layer of the membrane, and an absorption pad is connected to a downstream layer of the membrane. On the conjugate pad is dried a gold nanoparticle conjugate to which an antibody capable of being selectively bound to a sample substance is immobilized. On the membrane, an antibody selectively reacting with the sample substance and a substance capable of being bound to the antibody immobilized to a gold nanoparticle are immobilized at different locations. The antibody capable of being selectively bound to the sample substance and immobilized to the membrane, and the antibody immobilized to the gold nanoparticle are configured to be bound to the sample substance in a sandwich manner. The absorption pad is composed of a material capable of efficiently absorbing the fluid sample. In the LFA, when a fluid sample solution is dropped onto a sample pad, the antibody-gold nanoparticle conjugate having selectivity with respect to a sample and the antibody immobilized to the membrane are bound in the sandwich shape to form a band at an antibody-immobilized location on the membrane, which can be seen by the naked eye, if the sample is present on the sample pad.

However, a conventional LFA method provides a detection sensitivity of about 1 ng/mL of antigen protein and cannot be applied to a sample which requires higher detection sensitivity. In addition, for more convenient detection, it is necessary to reduce the volume of the sample and a measurement time.

Various membrane sensors are disclosed in the art, for example, "Membrane strip biosensor system for point-of-care testing" (Korean Patent No. 599420); "Composite membrane" (Japanese Patent Publication 2006-507511A); "Electrochemical membrane strip biosensor" (Korean Patent No. 348351); "Method for Determining Concentration of Multiple Analytes in a Single Fluid Sample" (U.S. Pat. No. 7,494,818); "Sensor having membrane and method for manufacturing the same" (Korean Patent No. 591390); "Test Device for Simultaneous Measurement of Multiple Analytes in a Single Sample" (U.S. Patent Publication No. 2005-214161), and the like. However, these publications do not suggest a technique capable of enhancing sensitivity of the sensor through adjustment of the sensitivity using a multi-hole film, detecting multi-component substances at the same time, and reducing a using amount of sample and analyte detection time through vertical injection of the sample.

The inventors of the present invention exerted all possible efforts to develop a high sensitivity membrane biosensor based on techniques, which have not been realized in the related art, and finally developed the present invention based on confirmation that a membrane biosensor prepared by joining a multi-hole film to a receptor-immobilized membrane permits rapid detection of analytes using a small amount of sample.

DISCLOSURE

Technical Problem

The present invention is directed to providing a high sensitivity membrane biosensor capable of detecting various kinds of immunological reactions or enzymatic reactions at the same time. The present invention is also directed to providing a method for measuring immunological reactions or enzymatic reactions using the high sensitivity membrane biosensor.

Technical Solution

An aspect of the present invention provides a membrane biosensor, which includes a multi-hole film having a plurality of holes and attached to the top of a membrane, to which receptors are immobilized at locations corresponding to the respective holes.

Another aspect of the present invention provides a membrane biosensor, which includes a multi-hole film having a plurality of holes and attached to the top of a membrane, receptors immobilized to the membrane at locations corresponding to the respective holes, and a conjugate pad formed on the multi-hole film.

A further aspect of the present invention provides a method for measuring immunological reaction using the membrane biosensor, which includes vertically injecting a sample into the membrane biosensor.

A further aspect of the present invention provides a method for measuring enzymatic reaction using the membrane biosensor, which includes vertically injecting a sample into the membrane biosensor.

Advantageous Effects

According to embodiments of the invention, the membrane biosensor allows adjustment of sensitivity of the membrane biosensor by adjusting a hole size of a multi-hole film, and may measure analytes with a high degree of sensitivity using a small amount of sample and various kinds of analytes by attaching various kinds of receptors to the membrane sensor.

Figure 1:
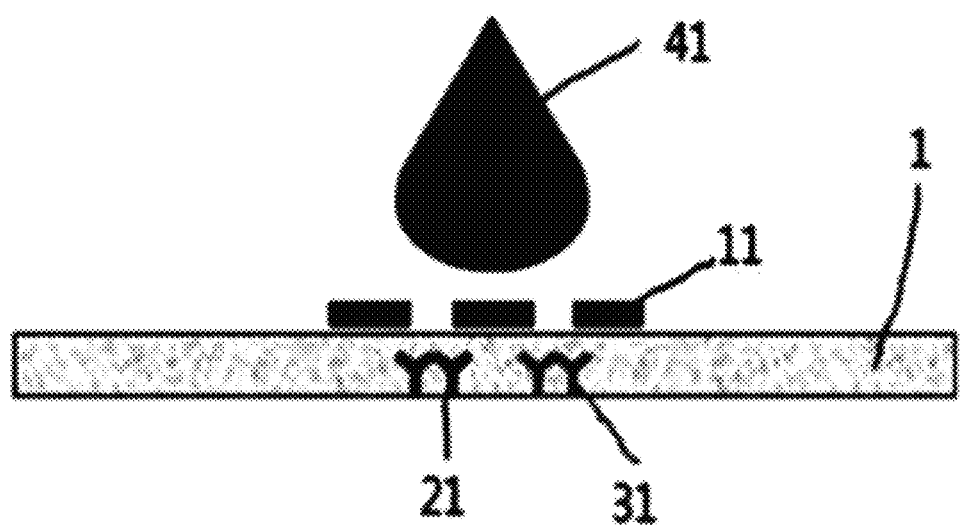
FIG. 1 is a view of one example of a membrane biosensor according to the present invention.

<Brief Description of Reference numerals of the Drawings>

| | |
|---|---|
| 1: Membrane | 11: Multi-hole film |
| 21, 31: Receptor | 41: sample |
| 51: conjugate pad | 61: Sample pad |
| T: portion to which cTnI antibody is immobilized as a receptor | |
| C: portion to which anti-mouse IgG is immobilized as a receptor | |
| B: portion to which BSA is immobilized as a receptor | |

BEST MODE

In one aspect, the present invention relates to a membrane biosensor, which includes a multi-hole film attached to the top of a membrane, to which receptors are immobilized (FIG. 1).

Figure 2:
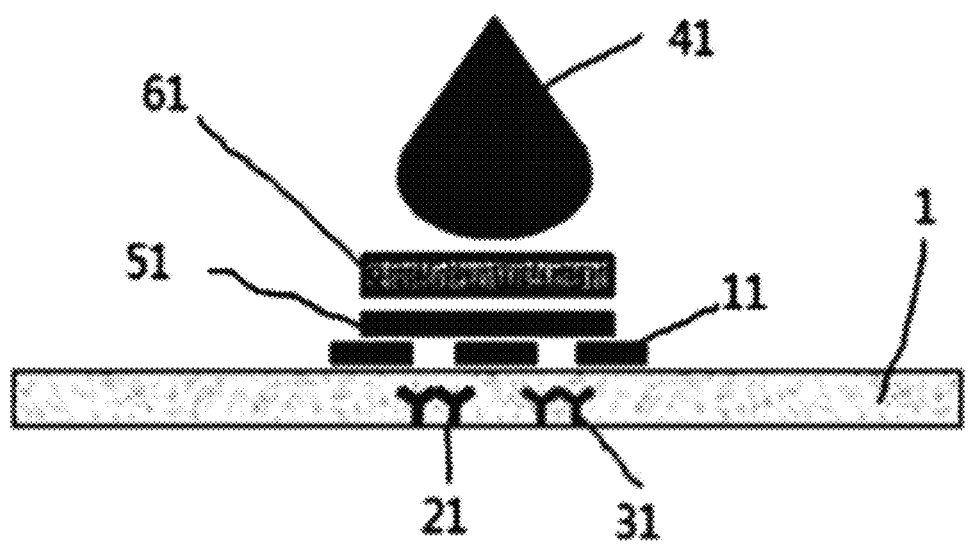
FIG. 2 is a view of another example of a membrane biosensor according to the present invention.

In another aspect, the present invention relates to a membrane biosensor, which includes a multi-hole film attached to the top of a membrane, to which receptors are immobilized, and a conjugate pad formed on the multi-hole film (FIG. 2).

According to the present invention, a biosensor is manufactured by attaching a multi-hole film to a membrane such that sensitivity of the sensor may be adjusted according to a hole size of the multi-hole film and multi-component analytes may be measured according to the number of holes in the multi-hole film. In addition, the membrane biosensor according to the present invention adopts a flow through hole (FTH) method in which a sample is dropped vertically to the sensor in measurement of immunological reaction or enzymatic reaction, thereby enabling measurement of the reaction in a short time using a small amount of sample.

As used herein, the term "multi-hole" means that an object has a plurality of holes, and the term "multi-hole film" means a film having a plurality of holes. As used herein, the term "hole" means an opening having a size capable of acting as a reaction well to allow a sample and a receptor to react therein.

According to the present invention, any suitable membrane capable of absorbing a sample solution may be selected by those skilled in the art.

In one embodiment of the invention, the membrane may be a nitrocellulose membrane. When a sample, for example, protein, is dropped onto the nitrocellulose membrane, the protein is immobilized to an initially dropped position instead of being significantly spread. Thus, when a sample is injected into holes of the multi-hole film bound to the top of the nitrocellulose membrane, the sample selectively reacts with receptors at portions of the membrane under the respective holes, allowing measurement of signals.

In this invention, receptors may be immobilized to the membrane by any suitable method including physical adsorption and chemical methods, which can be selected by those skilled in the art.

In this invention, the holes of the multi-hole film may have a size ranging from 10 μm to 5000 μm, without being limited thereto. Alternatively, the holes of the multi-hole film may have a size of 10~4000 μm, 10~3000 μm, 10~2000 μm, 10~4000 μm, 50~5000 μm, 50~4000 μm, 50~3000 μm, 50~2000 μm, 50~4000 μm, 100~5000 μm, 100~4000 μm, 100~3000 μm, 100~2000 μm, 100~4000 μm, 200~5000 μm, 200~4000 μm, 200~3000 μm, 200~2000 μm, or 200~4000 μm. The sensor has high sensitivity with decreasing hole size of the multi-hole film, since the sample reacts with the receptors in a smaller area. However, a hole size of less than 10 μm can obstruct the flow of a fluid sample, and a hole size of greater than 5000 μm can significantly reduce sensitivity of the sensor. Advantageously, the multi-hole film has a hole size ranging from 10 μm to 5000 μm in view of adjustment of sensitivity of the sensor.

According to the present invention, the multi-hole film may be made of a material allowing easy formation of the holes. For example, the multi-hole film may be composed of polymer, glass, elastomer, and silicone, without being limited thereto. Specifically, the multi-hole film may be made of polyimides, aluminum, polyacryls, polymethyl siloxane (PDMS), polyethylene (PE), polypropylene (PP), polystyrene (PS), polycarbonate (PC), polyvinyl chloride (PVC), and polymethyl methacrylate (PMMA), without being limited thereto.

According to the present invention, the multi-hole film may have a thickness ranging from 0.01 to 1 mm, 0.01 to 0.8 mm, 0.01 to 0.6 mm, 0.01 to 0.4 mm, 0.01 to 0.2 mm, 0.05 to 1 mm, 0.05 to 0.8 mm, 0.05 to 0.6 mm, 0.05 to 0.4 mm, or 0.05 to 0.2 mm, without being limited thereto.

According to the present invention, the multi-hole film may be an adhesive film having an adhesive deposited on one side thereof, which contacts the membrane. In this case, the multi-hole film is cut to a suitable size and placed on the membrane to attach the multi-hole film to the membrane. However, the present invention is not limited thereto, and any suitable process known in the art may be selected by those skilled in the art to attach the multi-hole film to the membrane.

According to the present invention, the receptor may selectively react with analytes. Specifically, the receptor may be selected from the group consisting of antibodies, antigens, enzymes, peptides, proteins, DNA, RNA, PNA (peptide nucleic acids), and aptamers.

As used herein, the term "selectively" refers to properties of two substances tending to specifically bind to each other and may be used together with "specifically".

According to the present invention, the sample applied to the membrane biosensor may include conjugates of a signal generator and a substance selectively bound to an analyte.

Namely, the sample applied to the membrane biosensor according to the present invention may be, for example, a certain sample containing or not containing an analyte, or a sample in which conjugates of a signal generator and a substance selectively bound to an analyte are mixed with the sample containing or not containing the analyte. In the former case, the conjugates of the signal generator and the substance selectively bound to the analyte may be separately injected into the membrane biosensor after injecting the sample. In the latter case, the sample may be applied to the biosensor essentially composed of the membrane and the multi-hole film without a separate conjugate pad or sample pad, and the conjugates of the signal generator and the substance selectively bound to the analyte are previously generated in the sample and are selectively bound to the receptors immobilized to the top of the membrane, thereby enabling detection of the analyte.

As used herein, the term "substance selectively bound to an analyte" refers to a substance having a specific binding reaction with the analyte, and may be selected from the group consisting of, for example, antibodies, antigens, enzymes, peptides, proteins, DNA, RNA, PNA (peptide nucleic acids), and aptamers. Further, the "substance selectively bound to an analyte" may be the same or different from the receptor immobilized to the membrane of the biosensor.

In the present invention, the signal generator may be metal nanoparticles, quantum dot nanoparticles, magnetic nanoparticles, enzymes, enzyme substrates, enzymatic reaction generators, chromophores, fluorescent substrates, or luminescent substrates.

When the signal generator is the metal nanoparticle, the analyte may be detected through color change of the metal nanoparticle resulting from selective reaction between the receptor and the analyte, and may be quantitatively analyzed by measuring absorbance, electrical conductivity, or the like of the conjugate of the metal nanoparticle and the analyte selectively bound to the receptor on the membrane. The metal nanoparticle may be, for example, gold nanoparticles, silver nanoparticles, or copper nanoparticles, without being limited thereto.

When the signal generator is the quantum dot nanoparticle, the analyte may be detected through fluorescence of the quantum dot nanoparticle resulting from selective reaction between the receptor and the analyte.

When the signal generator is the magnetic nanoparticle, the analyte may be detected through change of magnetic field resulting from selective reaction between the receptor and the analyte.

When the signal generator is an enzyme, enzyme substrate or enzymatic reaction generator, the analyte can be detected by measuring absorbance, fluorescence, or luminescence of a product by enzymatic reaction, since selective reaction between the receptor and the analyte causes enzymatic reaction such as oxidation-reduction reaction between the analyte or the receptor and the enzyme, enzyme substrate or enzymatic reaction generator. Examples of enzymes may include glucose oxidase, glucose dehydrogenase, alkaliphosphatase, and peroxidase, without being limited thereto. Examples of enzyme substrates may include glucose and hydrogen peroxide, without being limited thereto.

In addition, any suitable chromophores, fluorescent substrates, or luminescent substrates known in the art may be selected as the signal generator by those skilled in the art. In one embodiment of the invention, luminol may be used as the signal generator, without being limited thereto.

In this invention, when the analyte is a protein antigen, an antibody selective to the protein antigen is immobilized as the receptor to the membrane, and the sample may be a mixture of the protein antigen and a conjugate of the protein antigen-selective antibody and gold nanoparticles. Each of the antibody of the conjugate and the antibody immobilized to the membrane is selectively bound to the protein antigen acting as the analyte, and the gold nanoparticles are bound to the membrane at a position of the antibody immobilized to the membrane in a sandwich shape (antibody immobilized to membrane/protein antigen/antibody of the conjugate/gold nanoparticles of the conjugate), so that the analyte can be detected based on color change of the gold nanoparticles. At this time, when different receptors are immobilized to the respective holes of the multi-hole film, different analytes may be detected from the respective holes, thereby allowing measurement of multi-component analytes according to the number of holes.

In the membrane biosensor of the invention, a conjugate pad is formed on the multi-hole film, and a signal generator or a conjugate of a signal generator and a substance selectively bound to an analyte is deposited to and dried on the conjugate pad.

When the signal generator is deposited to and dried on the conjugate pad, and the signal generator is an enzyme, enzyme substrate or chemiluminescent substrate, the analyte may be measured by a signal from the signal generator caused by enzymatic reaction, which occurs by previously injecting or adsorbing the enzyme substrate or the enzyme reacting with the receptor and the signal generator to the top of the membrane, followed by injecting a sample. When the conjugate of the signal generator and the substance selectively bound to the analyte is deposited to and dried on the conjugate pad, the analyte is dropped vertically onto the membrane sensor analyte. Then, the analyte is sequentially bound to the "receptor-the analyte-the conjugate of the signal generator and the substance selectively bound to the analyte deposited to and dried on the conjugate pad" in this sequence, thereby allowing measurement of the analyte by a signal from the signal generator caused by selective reaction between the receptor and the analyte.

According to the present invention, the conjugate pad may be composed of any material which allows the conjugate to be easily separated from the conjugate pad when the conjugate pad is wetted by liquid after the conjugate is deposited to and dried on the conjugate pad. Any conjugate pad generally used for an LFA system may be used in the present invention.

According to the present invention, a sample pad may be formed on the conjugate pad. The sample pad serves to filter foreign matter from the analyte to provide more accurate measurement than the sensor without the sample pad. For example, when the analyte is blood, the sample pad serves to filter blood corpuscles or blood platelets from the blood (see FIG. 2). Any sample pad generally used for the LFA system may be used as the sample pad according to the present invention.

According to the present invention, a signal generator or a conjugate of a signal generator and a substance selectively bound to an analyte may be deposited to and dried on the sample pad.

In the present invention, a membrane for providing good flow of fluid may be inserted between the conjugate pad and the multi-hole film. In one embodiment, for example, any suitable membrane, such as a screen mesh (Zonyl FSN 100, SEFAR), a vivid membrane (Pall, Vivid Plasma Separation-GR), or the like, may be selected by those skilled in the art, without being limited thereto.

According to the present invention, the membrane may be divided into regions including the respective holes of the multi-hole film. In other words, in order to prevent the samples flowing under the respective holes of the multi-hole film from interfering with each other, the membrane may be divided into the regions, each of which includes a single hole. By division of the regions, the regions of the membrane disposed under the respective holes of the multi-hole film are separated from each other, and the samples flowing under the respective holes are not affected by each other, thereby improving measurement reproducibility.

Any suitable method known in the art may be used to divide the regions of the membrane. In one embodiment of the invention, a laser machining apparatus may be used to divide the regions of the membrane.

In a further aspect, the present invention relates to a method for measuring immunological reaction using the membrane biosensor. The method includes injecting a sample into the membrane biosensor in a vertical direction.

In yet another aspect, the present invention relates to a method for measuring enzymatic reaction using the membrane biosensor. The method includes injecting a sample into the membrane biosensor in a vertical direction.

For example, when measuring glucose, glucose oxidase and peroxidase are immobilized as receptors to the membrane under the multi-hole film, a conjugate pad on which a chromogen substrate of peroxidase (for example, luminol) is deposited and dried is formed on the multi-hole film, and a sample containing glucose is vertically dropped thereto. As a result, a hydrogen peroxide solution generated by the glucose oxidation enzyme and the color reaction substance induce luminescence by peroxidase, thereby allowing measurement of glucose.

According to the present invention, the membrane biosensor may measure and detect an analyte with high sensitivity in a short period of time using a small amount of sample by vertically injecting the sample into the membrane biosensor.

According to the present invention, the membrane biosensor may include different types of receptors immobilized to the respective holes of the multi-hole film. Thus, when a sample is vertically dropped onto the membrane biosensor, it is possible to simultaneously detect various analytes selectively binding to the different types of receptors immobilized to the respective holes of the multi-hole film.

Next, the present invention will be explained in more detail with reference to examples and comparative examples. It will be apparent to those skilled in the art that these examples are provided for illustrative purposes only and are not to be in any way construed as limiting the present invention.

Example 1

Manufacture of Membrane Biosensor and cTnI Analysis Using the Same 1-1. Synthesis of Gold Nanoparticle-Antibody Conjugate To 1 mL of a colloidal solution of gold nanoparticles (20 nm, BBInternational, GB), 0.1 mL of 0.1 M borate buffer (pH 8.5) and 10 µl of 1 mg/mL anti-cTnI antibody (Hytest, FIN) were added and reacted for 30 minutes. After reaction, 0.1 mL of 1% (w/v) BSA (Bovine serum albumin, Sigma, DE) in phosphate buffered saline (PBS, Gibco, USA) was added and reacted at room temperature for 15 minutes. Then, the resulting mixture was centrifuged at 10,000 rpm for 20 minutes at 4° C., followed by adding 1 mL of 1 mg/mL BSA solution in 10 mM PBS three times to precipitate and recover a gold nanoparticle-antibody conjugate, thereby obtaining a synthesized gold nanoparticle-antibody conjugate.

1-2. Manufacture of Membrane Biosensor

A nitrocellulose membrane (Millipore, 180 sec Nitrocellulose) was cut into a square having a size of about 2.5 cm×2.5 cm. Then, a 0.1 mm thick polyacryl double-sided tape was cut to a size of about 1 cm×1 cm, to which three holes having a diameter of about 0.4 mm were perforated to form a multi-hole film. The resulting multi-hole film was attached to the membrane.

As receptors, 0.1 mg/mL of cTnI antibody (anti-troponin I polyclonal antibody, Hytest, FIN), 0.1 mg/mL of anti-mouse IgG (Sigma, DE) and 1.0 mg/mL of BSA were injected in an amount of 0.50 each into the membrane through the respective three holes of the multi-hole film, and then dried. The membrane including the multi-hole film was wetted with BSA in a concentration of 1.0 mg/mL and then dried again, thereby obtaining a membrane biosensor comprising the multi-hole film.

1-3. cTnI Analysis

15 µl of hypothetical plasma (10 mM PBS, 1 mg/mL HSA, 10 mM EDTA-2Na) having cTnI dissolved in a concentration of 0, 0.1, 1 and 10 ng/mL and 10 µl of gold nanoparticle-antibody conjugate solution prepared in 1-1 of Example 1 were mixed and left for 10 minutes to prepare a sample solution. The sample solution was vertically injected into the multi-hole film of the membrane biosensor prepared in 1-2 of Example 1. The sample solution was injected into the membrane through the holes of the multi-hole film. In 3 minutes, almost all of the sample solution was injected into the membrane through the holes.

Figure 3:
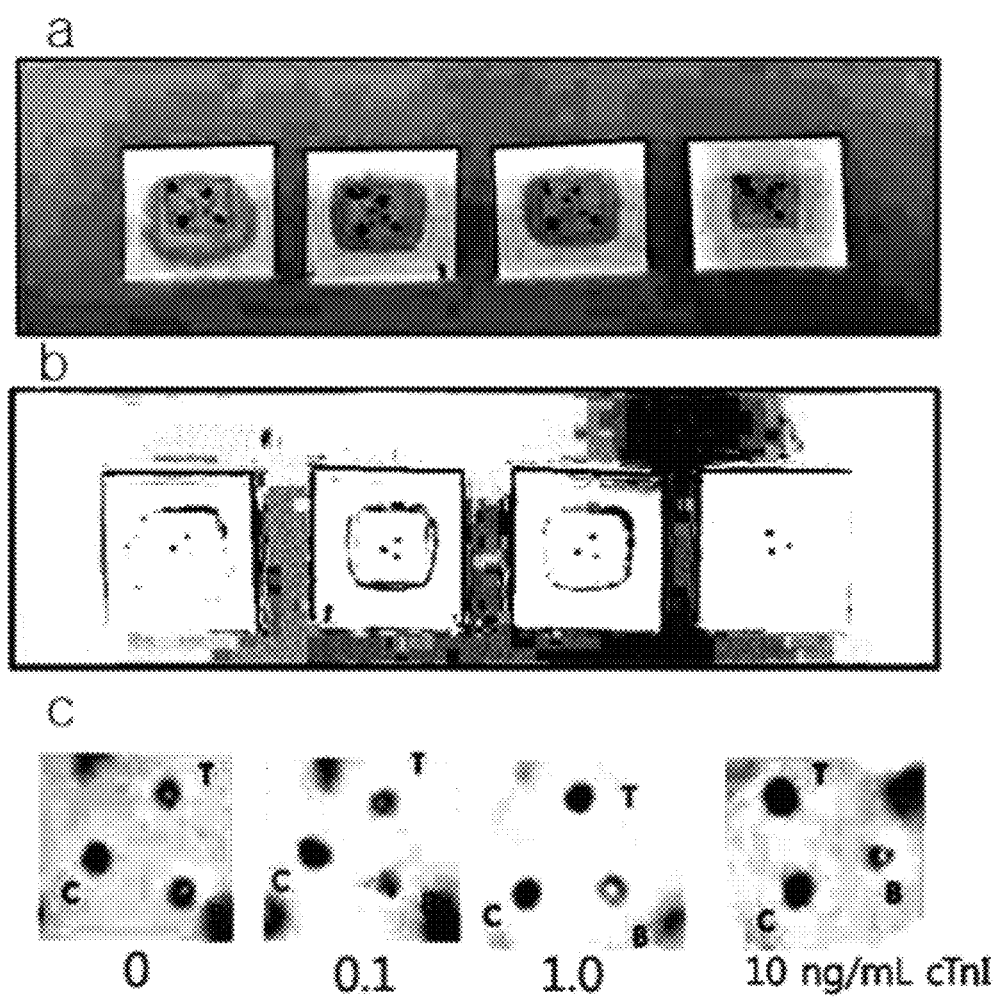
FIG. 3 shows images of analysis results obtained by injecting a sample into a membrane biosensor, to which three different receptors are immobilized, according to the present invention.

FIG. 3 shows images of a sample injected side (a) and an opposite side (b) of the sample injected side, and an enlarged image (c) of the opposite side of the sample injected side, as measured three minutes after the sample was injected. It can be seen that images of B (portion where BSA was immobilized as a receptor) and C (portion where anti-mouse IgG was immobilized as a receptor) were constant, whereas an image of T (portion where cTnI antibody polyclonal antibody was immobilized as a receptor) became darker with increasing concentration of cTnI.

In this regard, absorbance analysis was carried out as follows. Images were obtained after completion of reaction, and then the resultant values were analyzed using an image analysis program (Multigauge, Fuji Photo Film Co., Ltd). In signal analysis, average values of pixel intensities of both reaction portion (Signal) and background were calculated. Difference of both values was calculated and used as a final result value. The results of absorbance analysis are shown in Table 1.

TABLE 1

Absorbance analysis depending on cTnI concentration

| | cTnI concentration (ng/mL) | | | |
|---|---|---|---|---|
| | 0 | 0.1 | 1 | 10 |
| T | 11.27 | 11.53 | 23.23 | 30.4 |
| C | 19.95 | 24.23 | 19.23 | 24.82 |
| B | 10.81 | 11.11 | 10.08 | 10.73 |

Example 2

Manufacture of Membrane Biosensor and C-Reactive Protein (CRP) Concentration Analysis Using the Same 2-1. Synthesis of Gold Nanoparticle-Antibody Conjugate and Manufacture of Conjugate Pad To 1 mL of a colloid solution of gold nanoparticles (20 nm, BBInternational, GB), 0.1 mL of 0.1 M borate buffer (pH 8.5) and 10 µl of 1 mg/mL anti-CRP antibody (Abcam) were added and reacted for 30 minutes. After the reaction, 0.1 mL of 1% (w/v) BSA (Bovine serum albumin, Sigma, DE) in phosphate buffered saline (PBS, Gibco, USA) was added and then reacted at 4° C. for 60 minutes. After reaction, the resulting mixture was centrifuged at 10,000 rpm for 20 minutes at 4° C., followed by adding 1 mL of 1 mg/mL BSA solution in 10 mM PBS over three times to precipitate and recover a gold nanoparticle-antibody conjugate, thereby obtaining the synthesized gold nanoparticle-antibody conjugate. The synthesized gold nanoparticle-antibody conjugate was concentrated 2.5 times and the concentrated conjugate was injected in an amount of 10 µL each into the conjugate pad (Fusion 5, Whatman) cut to a size of about 7.5×3.5 mm, and then dried.

2-2. Manufacture of Membrane Biosensor

A nitrocellulose membrane (Millipore, 240 sec Nitrocellulose) was cut into a size of about 15 mm×15 mm and then lines in the form of T were drawn on the membrane. A 0.1 mm thick polyacryl double-sided tape was cut into a size of 10 mm×10 mm, and then two holes having a size of 0.5 mm were perforated on right and left sides to form a multi-hole film. The resulting multi-hole film was attached to the membrane. In this case, the two holes on the tape were placed on the right and left sides of T on the membrane. This arrangement of the holes was conducted such that the samples in the holes might not affect each other when the fluid samples passed through the two holes. As receptors, 5 µl of 0.2 mg/mL anti-CRP polyclonal antibody (Abcam) was injected into the membrane through one hole of the film attached thereto and 5 µl of 0.2 mg/mL anti-mouse IgG (Sigma) was injected into the membrane through the other hole. Subsequently, 5 µl of 10 mg/mL BSA in PBS buffer and 10 µl of PBS buffer were injected in this sequence and then dried. To the dried nitrocellulose membrane, a screen mesh (Zonyl FSN 100, SEFAR) cut into a size of 6×3 mm, a vivid membrane having a size of 7.5×3.5 mm, a conjugate pad (Fusion 5, Whatman) on which the gold nanoparticle-antibody conjugate prepared in Example 2-1 was dried, and a sample pad (Millipore) having a size of 7.5×3.5 mm were laminated in sequence to cover the holes of the membrane, thereby obtaining a biosensor.

2-3. CRP Analysis and Signal Analysis

50 µl of human plasma (CRP free serum) containing CRP dissolved in a concentration of 0, 0.01, 0.1, 1, 5 and 10 µg/mL was injected into the sensor and absorbance was measured over time.

Figure 4:
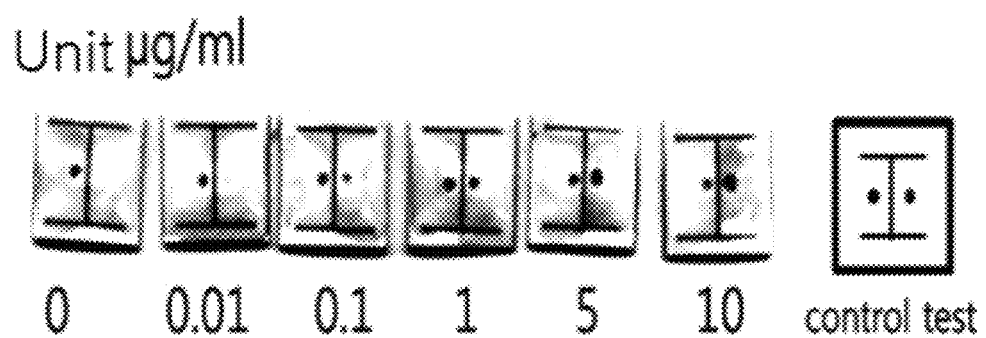
FIG. 4 shows images of CRP detection results using the membrane biosensor according to the present invention (Control: anti-mouse IgG immobilization, Test: anti-CRP polyclonal antibody immobilization).

From FIG. 4, it could be seen that all of the control areas (left, portions to which anti-mouse IgG was immobilized) showed high reactivity regardless of CRP concentration, while the test areas (right, portions to which anti-CRP polyclonal antibody was immobilized) showed an increase in signal intensity with increasing concentration when the CRP concentration was in the range of 0~5 µg/mL. Absorbance was analyzed in the same way as in 1-3 of Example 1. The results are shown in Table 2.

TABLE 2

Absorbance signal results depending on CRP concentration

| Concentration (µg/mL) | 3 minutes passed | 5 minutes passed | 7 minutes passed | 10 minutes passed |
|---|---|---|---|---|
| 0 | −3.61 | −3.12 | −4.28 | −3.1 |
| 0.01 | 1.15 | 1.31 | 2.03 | 2.79 |
| 0.1 | 16.47 | 20.79 | 22.81 | 29.42 |
| 1 | 41.85 | 43.89 | 52.4 | 52.49 |
| 5 | 74.17 | 75.91 | 81.02 | 81.07 |
| 10 | 60.21 | 63.05 | 60.66 | 60.9 |

Figure 5:
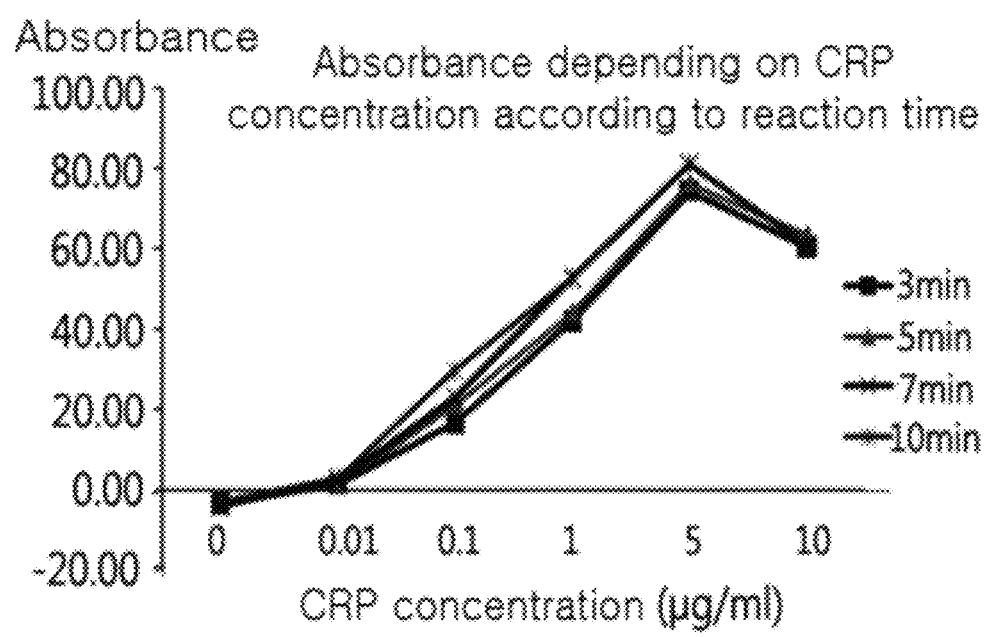
FIG. 5 is a graph depicting absorbance depending on CRP concentration according to reaction time as measured using the membrane biosensor according to the present invention.

It was observed from FIG. 5 that the absorbance signal intensity was increased over time, but reaction was completed after 3 minutes of an initial stage of the reaction and reaction absorbance of the completed reaction hardly changed even after 10 minutes. This demonstrates that measurement results can be rapidly obtained within approximately 3 minutes from the beginning of the reaction and that the reaction signal of the completed reaction is maintained for a certain period of time after completion of the reaction.

Figure 6:
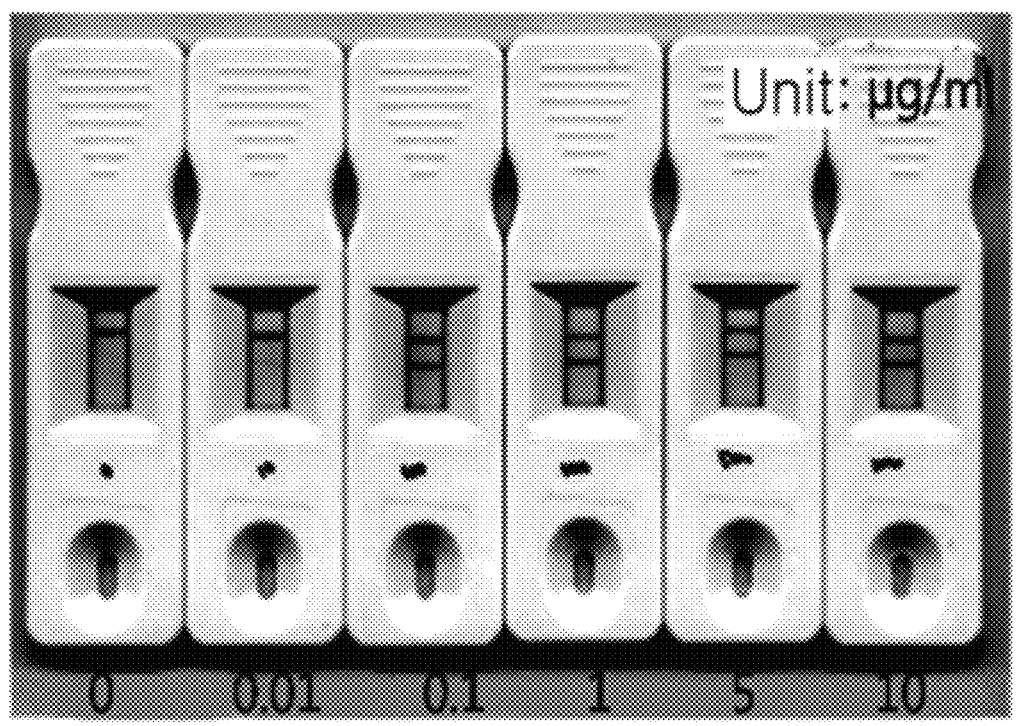
FIG. 6 shows images of CRP detection results using an LFA biosensor according to a comparative example.

In addition, as can be seen from FIG. 6, it is found that the biosensor according to the present invention has a much broader measurable scope than general LFA sensors. These results indicate that the sensor according to the present invention provides stable measurement results in a short period of time and a much broader scope than general sensors.

Comparative Example 1

Manufacture of LFA Biosensor and C-Reactive Protein (CRP) Concentration Analysis Using the Same 1-1. Synthesis of Gold Nanoparticle-Antibody Conjugate and Manufacture of Conjugate Pad Synthesis of the gold nanoparticle-antibody conjugate and manufacture of the conjugate pad were performed in the same way as in 2-2 of Example 2.

1-2. Manufacture of LFA Biosensor

A nitrocellulose membrane (Millipore, 180 sec Nitrocellulose) was cut into a size of 25 mm×300 mm and attached to an adhesive plastic card (Millipore) having a size of 300 mm×60 mm. Using a dispenser (Zeta Co., Ltd.), 1 mg/ml anti-mouse IgG (Sigma) was applied in a volume of 50 µl at a bed speed of 7.0 cm/second and a pump speed of 0.8 µl/cm to a control line within the nitrocellulose membrane, and 1 mg/ml anti-CRP polyclonal antibody (Abcam) was applied in a volume of 50 µl at a bed speed of 7.0 cm/second and a pump speed of 0.8 µl/cm to a test line within the nitrocellulose membrane. An absorbance pad (Millipore) was attached to the plastic card to overlap with the top of the nitrocellulose membrane by about 0.2 mm, and then cut into a size of 3.5 mm×60 mm. An Inter pad (MF1, Whatman) having a size of 3.8 mm×60 mm, a conjugate pad (fusion 5, Whatman) on which the gold nanoparticle-antibody conjugate was dried, and a sample pad (Millipore) were attached in this sequence to the plastic card to overlap with the bottom of the nitrocellulose membrane of the cut out structure by about 0.2 mm. The completed structure was inserted into an LFA case (Infopia) to obtain an LFA biosensor.

1-3. CRP Analysis and Signal Analysis

CRP signal was analyzed in the same way as in 2-3 of Example 2.

FIG. 6 shows, as CRP analysis results using the LFA biosensor, that CRP was detected at the CRP concentration in the range of 0.1~10 μg/mL. Absorbance analysis was performed in the same way as in 1-3 of Example 1. The results are shown in Table 3.

TABLE 3

| Concentration (μg/ml) | 10 minutes passed |
|---|---|
| 0 | 0 |
| 0.01 | 2.86 |
| 0.1 | 29.35 |
| 1 | 41.9 |
| 5 | 33.51 |
| 10 | 36.65 |

Figure 7:
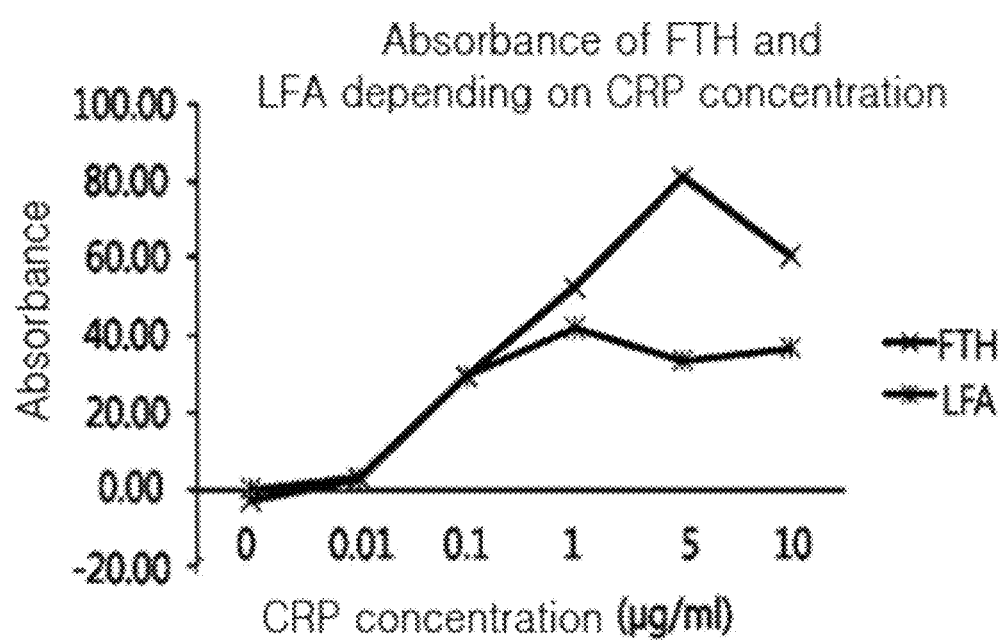
FIG. 7 is a graph depicting comparison results of absorbance depending on CRP concentration as measured using the membrane biosensor according to the present invention and the LFA biosensor (FTH: membrane biosensor according to the present invention, LFA: LFA biosensor).

As can be seen from FIG. 7, in the case where the CRP concentration was in the range of 0.1~10 μg/mL, the LFA sensor showed absorbance difference, which was not proportional to concentration. On the other hand, in the case where the CRP concentration was in the range of 0~5 μg/mL, the membrane sensor according to the present invention shows absorbance increasing with increasing concentration. Thus, it could be seen that, as compared with the LFAC sensor, the sensor according to the present invention had a much broader measurable scope regarding the concentration of the analyte and thus the sensor of the present invention could quantitatively detect the analyte more correctly and with good sensitivity. Accordingly, the sensor according to the present invention enables correct quantitative analysis by providing stable measurement results in a short period of time, a much broader measurable scope than general sensors and higher sensitivity than conventional LFA sensors.

Example 3

Manufacture of Membrane Biosensor and C-Reactive Protein (CRP) Concentration Analysis Using Enzymatic Chemiluminescence 3-1. Manufacture of Biosensor D-glucose (Duchefa Biochemie) and luminol (Sigma) were dissolved in 0.1M carbonate buffer (pH 9.0) to prepare a 50 mM solution, which was then injected in an amount of 20 μl each into the sample pad (Millipore) which had been cut into 7.5×3.5 mm, and dried. Anti-CRP antibody-peroxidase complex (Abcam) was dissolved in a PBS buffer to give a concentration of 20 μg/mL, and injected in an amount of about 7 μl into the vivid membrane (Pall, Vivid Plasma Separation-GR), which had been cut into about 7.5×3.5 mm, and then dried.

A nitrocellulose membrane (Millipore, 240 sec Nitrocellulose) was cut into a size of about 15×15 mm and lines in the form of ⊤ were drawn onto the membrane by means of a laser machining apparatus. A polyacryl double-sided adhesive tape having a thickness of 0.1 mm was cut into a size of 10×10 mm, and two holes having a size of 0.5 mm were perforated on left and right sides to form a film. The resulting film was attached to the membrane. In this case, the two holes on the adhesive were located at the left and right of ⊤ one by one. As receptors, 1 μl of a liquid mixture of 0.5 mg/mL anti-CRP polyclonal antibody (Abcam) and 250 U/mL of glucose oxidase (Sigma) was injected into the membrane through one hole of the film attached thereto and 1 μl of a liquid mixture of 0.5 mg/mL anti-mouse IgG (Sigma, DE) and 250 U/mL of glucose oxidase was injected into the membrane through the other hole. Subsequently, 5 μl of 10 mg/mL BSA in a PBS buffer and 10 μl of a PBS buffer were injected in this sequence and dried. A screen mesh (Zonyl FSN 100, SEFAR) cut into a size of 6×3 mm, a vivid membrane having a size of 7.5×3.5 mm on which the anti-CRP antibody-peroxidase complex prepared as above was dried, D-glucose prepared as above, and a sample pad (Millipore) on which luminol was dried were laminated in this sequence to the dried nitrocellulose membrane to cover the holes of the membrane, thereby obtaining a biosensor.

3-2. CRP Signal Analysis Using Luminescent Reaction

50 μl of PBS buffer having CRP dissolved in a concentration of 0, 0.01, 0.1, 1, 5 and 10 μg/mL was vertically injected into the sensor and luminescent signals over time were measured using a luminometer (LAS-3000, FUJI PHOTO FILM CO., LTD).

Figure 8:
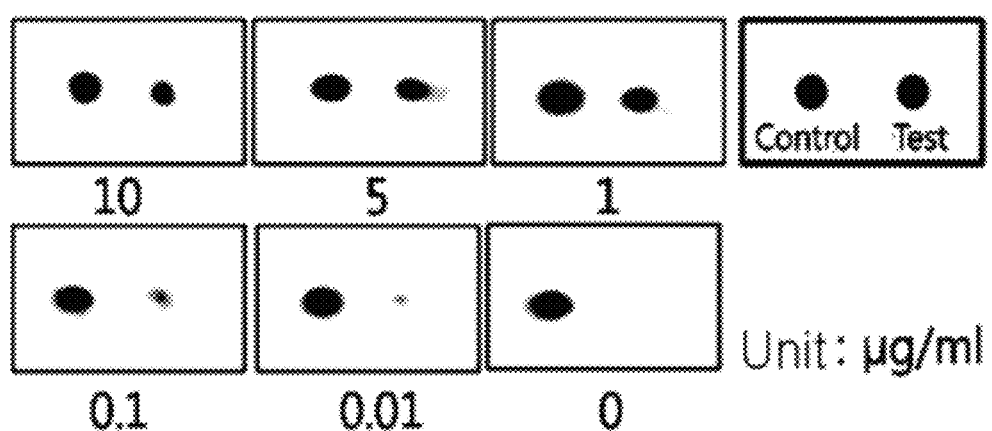
FIG. 8 shows images of CRP detection results by enzyme-chemiluminescence using the membrane biosensor according to the present invention (Control: anti-mouse IgG immobilization, Test: anti-CRP polyclonal antibody immobilization).

From FIG. 8, it could be found that the control areas (left, portions to which anti-mouse IgG was immobilized) showed high reactivity regardless of CRP concentration, while the test areas (right, portions to which anti-CRP polyclonal antibody was immobilized) showed an increase in signal intensity with increasing concentration when the CRP concentration was in the range of 0~1 μg/mL.

Figure 9:
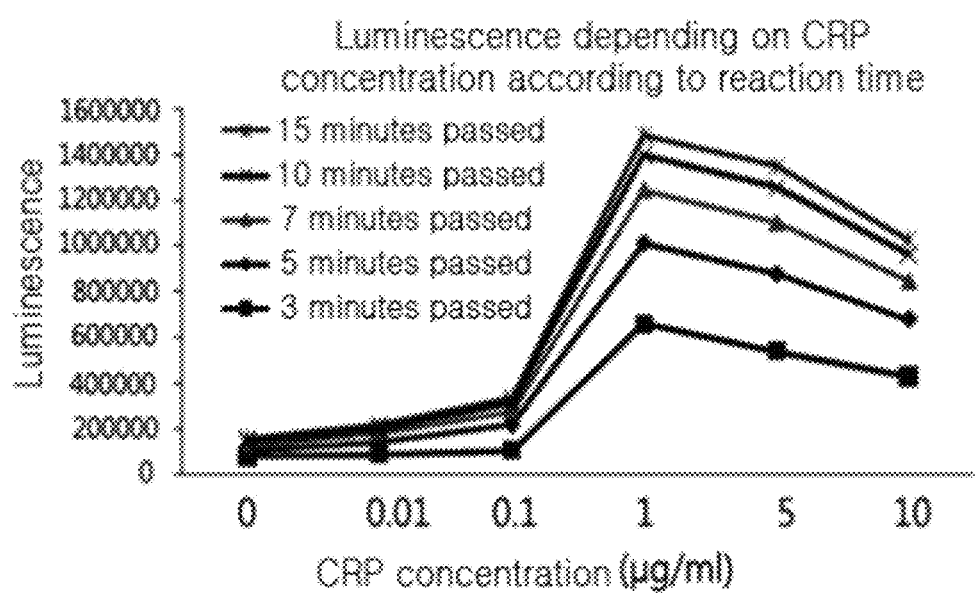
FIG. 9 is a graph depicting luminescence depending on CRP concentration according to reaction time by enzyme-chemiluminescence as measured using the membrane biosensor according to the present invention.
Figure 10:
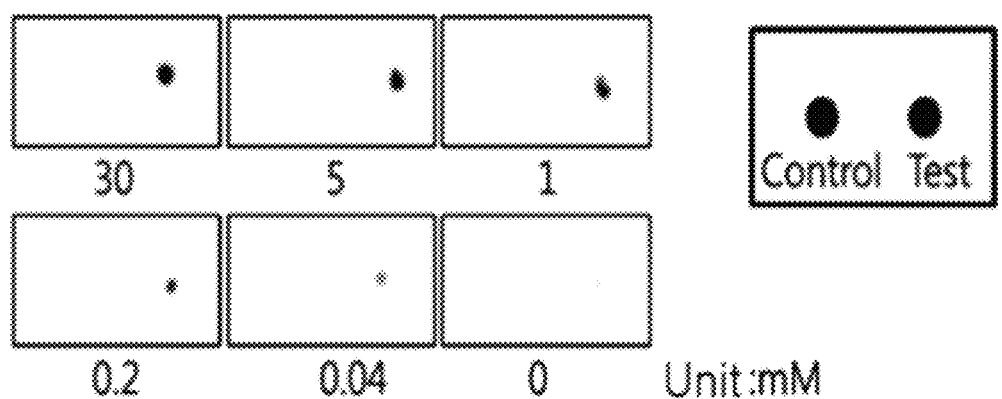
FIG. 10 shows images of D-glucose by enzyme-chemiluminescence as measured using the membrane biosensor according to the present invention (Control: only peroxidase immobilized, Test: glucose oxidase and peroxidase immobilized).

The degree of luminescence was analyzed and the results are shown in FIG. 9 and Table 4. It was found that although the luminescent signal increased over time, the disposition of signals itself is almost the same at 3 minutes and 15 minutes. Accordingly, it is determined that the test results can be detected within 5 minutes after sample injection.

TABLE 4

Luminescent signal results depending on CRP concentration

| Concentration (μg/mL) | 15 minutes passed | 10 minutes passed | 7 minutes passed | 5 minutes passed | 3 minutes passed |
|---|---|---|---|---|---|
| 0 | 78326 | 22490 | 28043 | 19214 | 10979 |
| 0.01 | 89538 | 52552 | 36381 | 24688 | 13710 |
| 0.1 | 106521 | 111455 | 54896 | 39408 | 23842 |
| 1 | 659558 | 350142 | 233597 | 154752 | 85941 |
| 5 | 540924 | 335252 | 224698 | 156162 | 91870 |
| 10 | 429909 | 249111 | 167023 | 114882 | 65047 |

Example 4

Manufacture of Membrane Biosensor and Analysis of D-Glucose in Human Serum Using Enzymatic Chemiluminescence 4-1. Manufacture of Biosensor Luminol (Sigma) was dissolved in 0.1M carbonate buffer (pH 9.0) to yield a 50 mM solution, which was then injected into the sample pad (Millipore) cut into a size of 7.5×3.5 mm in an amount of 20 μl each and dried.

A nitrocellulose membrane (Millipore, 240 sec Nitrocellulose) was cut into a size of about 15×15 mm and lines in the form of ⊥ were drawn onto the membrane by means of a laser machining apparatus. A polyacryl double-sided adhesive tape having a thickness of 0.1 mm was cut into a size of 10×10 mm, and two holes having a size of 0.5 mm were perforated on left and right sides one by one to form a film. The resulting film was attached to the membrane. In this case, the two holes on the adhesive were located at the left and right sides of ⊥ inscribed on the membrane. As glucosidases, 1 μl of a liquid mixture of 250 U/mL of glucose oxidase (Sigma) and 250 U/mL of peroxidase (Toyobo) was injected into the membrane through one hole of the film attached thereto and 1 μl of 250 U/mL of peroxidase solution was injected into the other hole, and then dried. A screen mesh (Zonyl FSN 100, SEFAR) cut into a size of 6×3 mm, a vivid membrane (Pall, Vivid Plasma Separation-GR) cut into a size of about 7.5×3.5 mm and a sample pad on which the luminol prepared as above was dried were laminated to the dried nitrocellulose membrane to cover the holes of the membrane, thereby obtaining a biosensor.

4-2. D-Glucose Signal Analysis Using Luminescent Reaction

50 μl of normal human serum (NHS) (Fitzgerald) containing D-glucose dissolved in a concentration of 0, 0.04, 0.2, 1, 5 and 30 mM was vertically injected to the sensor and the luminescent signal was measured 1 minute after the test sample injection using luminometer (LAS-3000, FUJI PHOTO FILM CO., LTD).

Figure 11:
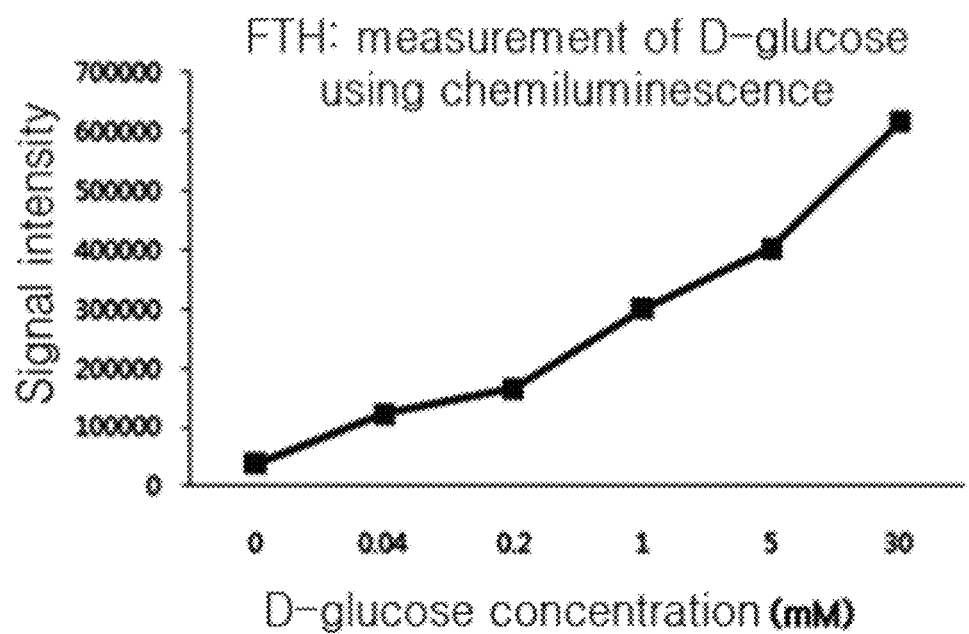
FIG. 11 is a graph depicting a degree of luminescence depending on the concentration of D-glucose detected by enzyme-chemiluminescence as measured using the membrane biosensor according to the present invention.

From FIG. 8, it could be found that the control areas (left, portions to which only peroxidase was immobilized) showed no reactivity regardless of D-glucose concentration, while the test areas (right, portions to which glucose oxidase and peroxidase were immobilized) showed increased luminescent signal with increasing concentration when the D-glucose concentration was in the range of 0~30 mM. FIG. 11 is a graph depicting an increase of luminescent signal with increasing D-glucose concentration.

Example 5

Manufacture of Membrane Biosensor and Comparison of Total Cholesterol Reaction at Level 1 and Level 2 of Control Serum Using Enzymatic Color Reaction 5-1. Manufacture of Biosensor A nitrocellulose membrane (Millipore, 240 sec Nitrocellulose) was cut into a size of about 15×15 mm and three circles having a diameter of 2 mm were drawn in a regular triangle arrangement using a laser machining apparatus. To each circle of the laser machined nitrocellulose membrane was injected 2 μL of a reaction solution to measure total cholesterol and then dried.

The composition and content of the reaction solution used to measure total cholesterol are as shown in Table 5.

TABLE 5

| Ingredients | Content (mg) |
| --- | --- |
| Cholesterol esterase (Toyobo) | 2.5 mg |
| Cholesterol oxidase (Toyobo) | 7.5 mg |
| Peroxidase (Toyobo) | 2.3 mg |
| MADB (Dojindo) | 8.72 mg |

TABLE 5-continued

| Ingredients | Content (mg) |
| --- | --- |
| 4-aminoantipyrine | 4.06 mg |
| BSA | 5 mg |
| Triton X-100 | 0.2 mg |
| MOPS (MP Biomedicals, LLC) | 10.45 mg |
| D.I water | 1 mL |
| pH | 5.0 |

A 0.1 mm thick double-sided adhesive tape was cut into a size of 10×10 mm and three holes having a size of 1 mm were perforated at the center of each circle to form a film. The film was attached to the dried membrane and a sample pad (Millipore) cut into a size of 5×5 mm was laminated, obtaining a biosensor.

5-2. Detection of Enzymatic Color Reaction Using Control Serum Level 1 and Level 2

50 μL of lipid control human serums Level 1 and Level 2 (Liquichek™, BIO-RAD) were injected into the manufactured biosensor to compare the degrees of luminescence of Level 1 and Level 2. The used control serums Level 1 and Level 2 are serums for controlling the degree of luminescence, wherein Level 1 comprises a normal range of cholesterol and Level 2 comprises an abnormal range of high concentration cholesterol.

Figure 12:
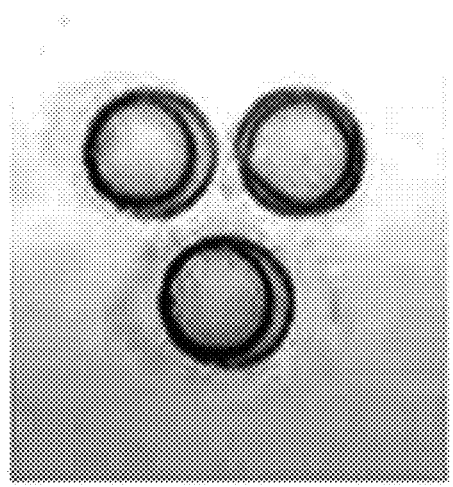
FIG. 12 shows images of measurement results of the concentration of total cholesterol of control serum based on enzymatic color reaction as measured using the membrane biosensor according to the present invention.
Figure 12:
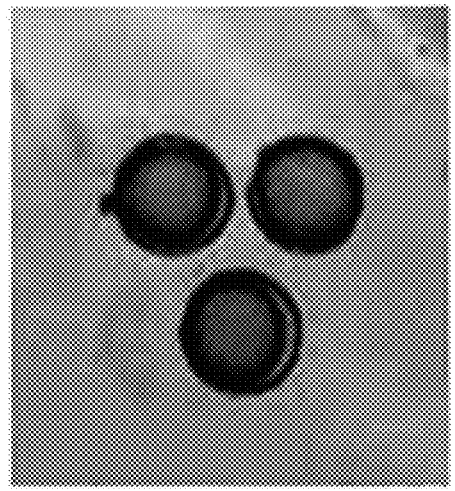

As can be seen from FIG. 12, it was found that the difference in color reaction at Level 1 and Level 2 was observed through color reaction. It was also found that the color of Level 2 sample with a higher concentration of total cholesterol was darker.

Although some exemplary embodiments have been described with reference to the accompanying drawing, it will be understood by those skilled in the art that these embodiments are provided by way of illustration only and do not limit the scope of the present invention. Therefore, the scope and sprit of the present invention should be defined by the accompanying claims and equivalents thereof.

The invention claimed is:

1. A membrane biosensor comprising:
a film comprising a plurality of holes, wherein the film is attached to a top of a membrane, and each hole of the plurality of holes is separated from adjacent holes of the plurality of holes;
receptors immobilized at locations on the membrane; and
a conjugate pad on the film,
wherein a location of each receptor of the receptors is defined by a corresponding hole of the plurality of holes,
wherein the holes have a size ranging from 10 to 5000 μm.

2. The membrane biosensor of claim 1, wherein the receptors are selected from the group consisting of antibodies, antigens, enzymes, peptides, proteins, DNA, RNA, PNA (peptide nucleic acids), and aptamers.

3. The membrane biosensor of claim 1, wherein the membrane is a nitrocellulose membrane.

4. The membrane biosensor of claim 1, wherein the conjugate pad is deposited with a signal generator, or a conjugate of a signal generator and a substance selectively bound to an analyte.

5. The membrane biosensor of claim 1, further comprising: a sample pad formed on the conjugate pad.

6. The membrane biosensor of claim 1, further comprising: a membrane inserted between the conjugate pad and the film to provide good fluid flow.

7. The membrane biosensor of claim 1, wherein the membrane is divided into a plurality of regions including each hole of the film.

\* \* \* \* \*